United States Patent [19]

Rubino et al.

[11] Patent Number: 5,558,858
[45] Date of Patent: Sep. 24, 1996

[54] CO-DRIED ALUMINUM OXYHYDROXIDES

[75] Inventors: Andrew M. Rubino, Chatham; Arthur A. Siciliano, Denville, both of N.J.

[73] Assignee: Reheis, Inc., Berkeley Heights, N.J.

[21] Appl. No.: 586,333

[22] Filed: Sep. 17, 1990

Related U.S. Application Data

[63] Continuation of Ser. No. 289,687, Sep. 3, 1981, abandoned.

[51] Int. Cl.$^6$ ............................................. A61K 7/32
[52] U.S. Cl. .................................................... 424/68
[58] Field of Search ................................................ 424/68

[56] References Cited

U.S. PATENT DOCUMENTS

| | | | |
|---|---|---|---|
| 1,621,528 | 3/1927 | Ellis | 423/495 |
| 2,196,016 | 4/1940 | Huehn et al. | 424/68 UX |
| 2,256,505 | 9/1941 | Thompson | 424/68 |
| 2,350,047 | 5/1944 | Klarmann et al. | 424/68 X |
| 2,373,198 | 4/1945 | Roehrich | 424/68 X |
| 2,392,153 | 1/1946 | Kastning | 424/68 X |
| 2,459,289 | 1/1949 | Roehrich | 424/68 |
| 2,944,914 | 7/1960 | Bugosh | 424/68 X |
| 3,014,055 | 12/1961 | Johnson | 424/68 X |
| 3,259,545 | 7/1966 | Teller | 424/68 X |
| 3,499,963 | 3/1970 | Rubino | 424/157 |
| 3,599,150 | 8/1971 | Feinberg | 424/88 |
| 4,112,072 | 9/1978 | Rubino et al. | 424/157 |
| 4,115,553 | 9/1978 | Rubino | 424/155 |

OTHER PUBLICATIONS

E. A. Vlasov et al., "Influence of Organic Substances on Formation of the Porous Structure of Active Alumina," *Journal of Applied Chemistry of the U.S.S.R.*, pp. 1920–1921, Sep., 1976.

"A Vehicle For Stabilizing Aluminum Hydroxide Gel", by Kerkof, N. J.; Hem, S. L. and White, J. L., Journal Of Pharmaceutical Sciences, 75, vol. 64, No. 12, pp. 2030–2032, Dec. 1975.

*Primary Examiner*—C. Warren Ivy
*Assistant Examiner*—Evelyn Huang
*Attorney, Agent, or Firm*—Panitch Schwarze Jacobs & Nadel, P.C.

[57] ABSTRACT

Adsorptive, protein-binding aluminum oxyhydroxides are prepared by mixing carbonate-free, highly hydrated, aluminum oxyhydroxide containing aqueous suspensions with water soluble additives that furnish coordinating moieties with the aluminum compound and drying the resultant mixture. The protein-binding aluminum oxyhydroxides can be made resuspendable by acidifying to a pH value of between about 4 and about 6.5. Such acidification can occur either before or after drying.

13 Claims, 1 Drawing Sheet

CO-DRIED ALUMINUM OXYHYDROXIDES

CROSS-REFERENCE TO RELATED APPLICATION

This application is a continuation of our application Ser. No. 289,687, filed Aug. 3, 1981, now abandoned.

BACKGROUND OF THE INVENTION

This invention relates to the co-drying of highly hydrated, relatively inert, carbonate-free aluminum oxyhydroxide suspensions. The suspensions are useful as adsorptive, protein-binding agents. Furthermore, one aspect of this invention relates to resuspendable, adsorptive, protein-binding agents. This invention also concerns topical skin compositions utilizing the agents produced in accordance with this invention.

It is well known to those skilled in the art that aluminum hydroxide gels are irreversibly degraded upon drying. The dehydration processing effectuates the loss of "water-of-constitution", among other entities, resulting in the destruction of most of the positive attributes characteristic of such gels, which properties serve as the very basis of their use in many applications. Illustrative degradative changes which can result are the following:

(1) alteration of the physiochemical structure of the products affecting their surfaces as well as their chemical reactivities;

(2) loss of adsorbent capacity;

(3) impairment of suspendability;

(4) increased density;

(5) increased particle size; and (6) reduced viscosity.

The degradation of aluminum hydroxide gels upon dilution with water is discussed in "A Vehicle For Stabilizing Aluminum Hydroxide Gel" by Kerkhof, N. J.; Hem, S. L. and White, J. L., JOURNAL OF PHARMACEUTICAL SCIENCES, 75, Vol. 64, No. 12, pp. 2030–2032, Dec. 1975.

U.S. Pat. Nos. 4,112,072 and 4,115,553 are directed to producing dried antacids. These patents describe the codrying of certain basic reactive aluminum bicarbonate-carbonate compounds with polyols to form novel antacid tablets.

U.S. Pat. No. 3,599,150 concerns a freeze stable suspension of an aluminum hydroxide gel. The suspension has an alum-precipitated aqueous extract or aqueous pyridine extract of an antibody producing antigenic substance absorbed thereon in an aqueous solution containing a water-soluble non-toxic polyhydric alcohol and water-soluble non-toxic polymers. This patent, however, is not concerned with co-drying of the aluminum hydroxide gel.

Non-reactive aluminum oxyhydroxides in the wet state, i.e., suspended in water, are known as good adsorbers. For example, such suspensions are used in vaccines as toxin adsorbers (an adsorbent is a material that attracts and holds to its surface a gas, liquid, or solid ). Heretofore, these gels were useful only in the wet state. It was recognized that it was uneconomical to "ship large quantities of water around" with the aluminum hydroxide and that it would be advantageous to concentrate the aluminum hydroxide and resuspend it when needed. Attempts to dry such suspensions in order to concentrate them have heretofore not met with success due to the degradation upon drying of aluminum hydroxide as discussed above.

Heretofore, there has been no teaching of co-drying an inactive aluminum oxyhydroxide gel to produce an adsorptive, protein-binding agent. Furthermore, no such agent has heretofore been produced with sufficient resuspendability properties.

SUMMARY OF THE INVENTION

There has now been discovered a method to produce adsorptive, protein-binding aluminum oxyhydroxides. Further, there has now been discovered a method to produce absorptive, protein-binding, resuspendable aluminum oxyhydroxides.

A carbonate-free highly hydrated, aluminum oxyhydroxide containing aqueous suspension which is relatively inert towards alkalis and acids is mixed with a water soluble additive. The additive furnishes coordinating moieties with aluminum. The resulting mixture is then dried to form solid particles.

A resuspendable, protein-binding, absorptive aluminum oxyhydroxide is prepared by acidifying the aluminum oxyhydroxide-additive mixture. Such acidification can be conducted either when the aluminum oxyhydroxide is in aqueous suspension, or after the mixture has been dried. If acidified after drying, the solid particles are mixed with water prior to the introduction of acid. In all cases, acidification is conducted to yield a pH value of between about 4 and about 6.5.

DETAILED DESCRIPTION OF THE INVENTION

The present invention relates to co-drying carbonate-free, highly hydrated, aluminum oxyhydroxide suspensions which are relatively inert towards weak alkalis and acids in such a manner as to minimize or totally avoid degradation of the suspensions. The aluminum oxyhydroxide compounds that can be utilized in this invention include any inert aluminum hydroxide in which only the aluminum and the hydroxy and/or oxy entities are present, such as, for example, boehmite (alpha alumina monohydrate) and diaspore (beta alumina monohydrate). These compounds are distinguished from "reactive-grade aluminum hydroxide" which contain carbonate/bicarbonate. Such reactive compounds which find wide use as antacids, inter alia, are distinguished from inert aluminum hydroxide by simple carbon dioxide evolution analysis.

The additive mixed with the aluminum oxyhydroxide must be capable of furnishing coordinating moieties with aluminum and also must be soluble in water. If the product of the co-drying method of the present invention is to be utilized as an agent in a skin composition, the additive must further be topically acceptable, i.e., safe for use on the skin.

The additive can be an alcohol, sugar, amino acid, polysaccharide or polyfunctional nitrogen containing compound.

Non-limiting examples of suitable alcohols, i.e. polyhydric compounds, for use in the present invention as additives include glycerol, sorbitol, mannitol, polyethylene glycol (Carbowax), polypropylene glycol, butylene glycol and xylitol.

Non-limiting examples of suitable sugars that can be used as additives in the present invention include lactose, sucrose and glucose.

Non-limiting examples of suitable polyfunctional nitrogen containing compounds that may be used as additives in this invention include amino acids, such as L-glutamic acid; urea; glycine and beta-alanine. Use of amino acids of suitable strengths, i.e. concentrations, would allow the use of such acids to serve the dual function as an additive and acidifier when a resuspendable product is desired.

Non-limiting examples of polysaccharides that may be utilized as additives in the present invention include corn starch, "VEEGUM", "CERULOSE", "CARBOPOLS" and "CELLOSIZE".

The weight ratio of aluminum oxyhydroxide, calculated as aluminum oxide to additive present in the suspension prior to drying, ranges between about 10:1 and about 3:2, more particularly between about 6:1 and about 3:2. Based on the product, after drying, the additive can amount to between about 5 weight percent and about 30 weight percent of total product. The point of determination for the amount of additive, either before or after drying, is not per se critical and only has significance when volatile additives are utilized. A volatile additive will dissipate to some degree during drying depending on its volatility and the drying temperature. The weight ratios of additive to aluminum oxide as given above assume no loss of additive during drying. It would be a simple matter for one practicing this invention to calculate the estimated loss of additive due to evaporation and then add extra additive in anticipation of such loss. For a non-volatile additive such as corn starch, the foregoing procedure would be unnecessary.

The mixture of additive and aluminum oxyhydroxide compound is subjected to co-drying at appropriate temperatures. High drying temperatures, however, should not be utilized since there is a tendency to break bonds at high temperatures. It is advantageous to drive-off as much moisture as possible without over-drying the mixture. It is preferred to dry the mixture to attain between about 55 weight percent and about 65 weight percent aluminum oxyhydroxide, as calculated as aluminum oxide.

Any convenient drying method can be employed, such as, for example, spray drying, vacuum drying and hot air circulating ovens. The type of drying utilized will generally determine the particle size of the resultant solids. It is preferred in many instances to form a fine powder. Such powder can, for example, be produced using spray drying techniques or other drying techinques producing larger particles which are subsequently-comminuted via various grinding techniques known in the art.

Although it is usually desired to minimize the amount of additive, such amount is directly proportional to protein-binding capacity. Protein binding is enhanced by increasing the surface area of the aluminum containing compound particles, i.e., fine particle size. The suspendability of the dried products of this invention are inversely proportional to the pH of their respective suspensions.

The more concentrated the product, the less expensive the shipping costs due to elimination of unnecessary water being carried along with the useful product. Thus it is advantageous to use a product that is readily resuspendable with water.

To obtain a protein-binding, adsorptive agent that is resuspendable, acid must be utilized. Acidification can be conducted either prior to co-drying or after codrying. It is preferred to acidify prior to co-drying in order to produce a concentrated resuspendable solution. In such case, the aluminum oxyhydroxide in aqueous suspension is acidified to yield a pH value for the suspension of between about 4 and about 6.5, more particularly between about 5 and about 6. The acidified suspension is then mixed with the additive and co-dried to the desired degree. Alternatively, the aluminum oxyhydroxide aqueous suspension can be mixed with additive and then acidified to the pH range as given above prior to co-drying. The acidification can be conducted with any moderately strong acid such as, for example, hydrochloric acid, nitric acid and sulfuric acid, just to name a few. Acidification can also be carried out with compounds which yield acids upon hydrolysis such as $AlCl_3$.

Moreover, acidification can be conducted after co-drying. In such case, the co-dried product is mixed with water, preferably to form a suspension and acidified to the pH range as given above.

The adsorptive, protein-binding aluminum oxyhydroxide agent produced by the method of the present invention can be employed in topical skin compositions. It can be used alone or in combination with other ingredients to form useful compositions for such products as sun screens, wrinkle fillers, acne medications, poison ivy remedies, burn remedies, anti-fungicides, antiseptics, analgesics, cosmetics, for example, lipsticks, makeup, and skin creams, just to name a few. Such other ingredients utilized in conjunction with the product of the present invention to form topical skin compositions include emulsifiers, such as the combination of glycerol monostearate, triethanolamine and stearic acids; thickeners such as stearic acid; emollients such as isopropyl myristate and humectants such as glycerine. Typical formulations are given as follows:

| Co-Dried Powder Produced In Accordance With The Present Invention - Approximate Analysis | |
|---|---|
| wt. % $Al_2O_3$ | 60.10 |
| wt. % Glycerine | 17.30 |
| wt. % Chloride | 3.40 |
| wt. % Na | 0.45 |
| wt. % $SO_4$ | 0.71 |
| wt. % Water | 19.04 (some water may exist as $OH^-$) |
| pH (4% Suspension) | 5.1 |
| Bulk Density | 0.77 g/cc |
| Protein Binding Capacity | 1.50 mg/mg $Al_2O_3$ at pH 5.5 |

| Ointment | |
|---|---|
| $Al_2O_3$ - Glycerine Powder as given above | 3.2 wt. % |
| Mineral Oil | 15.0 wt. % |
| Petrolatum | 76.8 wt. % |
| Polyoxethylene 4 Sorbitan Monostearate ("TWEEN 61") | 5.0 wt. % |

| Powder | |
|---|---|
| $Al_2O_3$ - Glycerine Powder as given above | 3.2 wt. % |
| Talc | 93.8 wt. % |
| Magnesium Stearate | 3.0 wt. % |

| Creams | wt. % | wt. % |
|---|---|---|
| $Al_2O_3$ - Glycerine Powder as given above | 5.0 | 5.0 |
| "ARLACEL 165" (Glycerol Monostearate and Polyoxyethylene Stearate) | 3.5 | 3.5 |
| Mineral Oil | 5.0 | 3.0 |
| Isopropyl Myristate | 3.0 | 6.0 |
| Propylene Glycol | 2.0 | 1.0 |
| Cetyl Alcohol | 1.5 | 4.0 |
| Methyl Paraben | 0.2 | 0.2 |
| Propyl Paraben | 0.05 | 0.05 |
| "MYRJ 52" (Polyoxyethylene 40 Stearate) | — | 0.5 |
| Titanium Dioxide | — | 0.2 |
| Deionized Water | 79.75 | 76.55 |

The present invention produces an aluminum oxyhydroxide agent having the following attributes:

(1) oil absorption (an absorbent is a material that "sucks up" or incorporates liquids, gases, etc.)

(2) thixotropic;
(3) protein-binding
(4) resistant to being washed away;
(5) esthetically pleasant;
(6) stable;
(7) non-tacky;
(8) non-greasy;
(9) non-irritating;
(10) non-toxic;
(11) compatible with oxidizing agents, for example, hydroperoxide and benzoperoxide;
(12) having a broad pH range; and
(13) resuspendable (when acidified).

The invention is further described by reference to the following specific, non-limiting examples.

EXAMPLES 1–10

Effect of Glycerol Levels on Resuspendability of Co-Dried Products

Examples 1–5 (without HCl)

Five different $Al_2O_3$/glycerol weight ratio levels were utilized for examination of resuspendability: 3/0, 6/1, 3/1, 2/1, 1.5/1. To each batch of $Al_2O_3$, glycerol was added according to the formula:

$$\frac{(\text{wt. } Al_2O_3)\ (\%\ Al_2O_3 \text{ gel})\ (0.01)}{\text{Ratio } Al_2O_3/\text{glycerol desired}}$$

The source for $Al_2O_3$ used throughout all the examples herein was Reheis Chemical Company "F-5000" gel. "F-5000" is a carbonate-free, highly hydrated, aluminum oxyhydroxide gel which is relatively inert towards weak alkalis and acids.

5500 grams of 9.6 wt.% $Al_2O_3$ were added to an 18 liter Nalgene polypropylene vessel. Ten liters of well water were added to the gel and the mixture was homogenized with a Premier dispersator for two hours. From this slurry, five aliquots of 3000 grams each were taken, and each was placed in an 8 liter Nalgene polypropylene vessel.

Example 1

To the first aliquot was added 17.1 grams of glycerol according to the above formula. The slurry was agitated for an hour and screened through a #40 sieve before spray drying. Before the slurry was spray dried, two liters of well water were added to the slurry to improve pumpability. The slurry was spray dried at 120°–125° C. in a 3 foot circular Bowen spray dryer employing a two-fluid nozzle head. Air pressure was set at 80 psig and feed rate at 100 ml/min. This procedure yielded about 150 grams of finely divided, free-flowing, white powder with a pre-spray dry $Al_2O_3$ to glycerol rate of 6/1 (see Table 1).

To demonstrate the resuspendability of the $Al_2O_3$-glycerol co-dried system with HCl, 2 grams of the above powder was added to 25 grams deionized water in a 4"×1" glass vial. With its cap in place, the vial was shaken ten times and three drops (approximately 0.14 grams) of 31% HCl was added to the vial by a medicine dropper. The vial was again shaken ten times. The vial approximated 4 wt % $Al_2O_3$ (Example 1A). Resuspendability of an 8% system was also tested using 4 grams of powder and 5 drops (approximately 0.24 grams) of 31% HCl in 25 grams deionized water (Example 1B).

After standing overnight, the pH's of the vials were measured with a Beckman SS-3 pH meter standardized at pH 5 and pH 7.

Example 2

This example is identical to the above Example 1 with the exception that 34.1 grams of glycerol were added to the slurry for a projected 3/1 ratio of $Al_2O_3$ to glycerol. Spray drying parameters and resuspendability techniques for 4% and 8% resuspensions were identical to Example 1 and for succeeding Examples 3–5.

Example 3

In this example 51.2 grams of glycerol was used to achieve a 2/1 ratio of $Al_2O_3$ to glycerol.

Example 4

In this example 68.2 grams of glycerol was used with the resultant slurry having a 3/2 ratio of $Al_2O_3$ to glycerol.

Example 5

No glycerol was used in this slurry which served as the 3/0 control.

The above spray dried slurries were analyzed for % $Al_2O_3$ and reported in Table I herein.

Resuspendability of the $Al_2O_3$-glycerol co-dried systems with HCl added on resuspension is shown in Table II herein.

Examples 6–10 (with HCl)

5000 grams of 9.6 wt.% $Al_2O_3$ were added to an 18 liter Nalgene polypropylene vessel. To this, three liters of well water were added. The pH of the slurry was then adjusted to 4.8 with 62 ml of 31% HCl under constant agitation with a Premier dispersator. The mixture was homogenized for two hours. From this slurry, five aliquots of 1800 grams each were taken and placed in an 8 liter Nalgene polypropylene vessel.

Example 6

To the first 1800 gram aliquot was added 18 grams of glycerol under constant agitation with the dispersator. The slurry was agitated one hour, and then screened through a #40 mesh sieve before spray drying (No extra well water was added to the slurry since it was pumpable). The spray drying parameters followed exactly those enumerated above in Example 1. 130 grams of finely divided, free-flowing powder resulted with a 6/1 pre-spray dry $Al_2O_3$ to glycerol ratio (see Table II).

Resuspendability of this system was achieved by adding 2 grams of the powder to 25 grams deionized water in a 4"×1" glass vial. The vial was shaken ten times and left to stand overnight. After a minimum of 24 hours, pH's and descriptions were recorded.

Example 7

This example was identical to Example 6 except 36 grams of glycerol was added to the slurry to yield a 3/1 ratio. Dilution, spray drying parameters and resuspendability techniques for 4% resuspensions were identical to Example 6 for this and the succeeding Examples 8 through 10.

Example 8

The third aliquot received 54 grams of glycerol for an $Al_2O_3$/glycerol ratio of 2/1.

Example 9

72 grams of glycerol were added to the fourth 1800 gram portion for a 3/2 ratio $Al_2O_3$ to glycerol.

Example 10

To the last aliquot of slurry, no glycerol was added.

The spray dried slurries in each of the above Examples 6–10 produced 130–140 grams of finely divided, free-flowing, white powder. Analyses of these powders is given in Table III herein.

Table IV given herein describes resuspendability of the $Al_2O_3$-glycerol-HCl system at various glycerol concentrations.

Examples 11–15

Effect of pH on Resuspendability

In the following examples, the effect of pH on $Al_2O_3$-glycerol-HCl co-dried systems is demonstrated. Varying amounts of HCl was used prior to spray drying to achieve powders of different pH values.

To 6000 grams of 9.6% $Al_2O_3$ gel in an 18 liter Nalgene polypropylene vessel was added 3600 grams of well water and the resultant mixture was slurried with a Premier dispersator for two hours. This slurry was then split into five 1800 grams aliquots each and put into 8 liter Nalgene polypropylene vessels. Each of the five portions was acidified to a different extent as shown in Examples 11 through 15.

Example 11

To the first 1800 gram aliquot was added 36 grams glycerol and 15.7 ml 31% HCl under constant agitation from a dispersator. The pH was measured and found to be 4.3. 130 grams of finely divided, free-flowing, white powder resulted after spray drying at parameters mentioned in Example 1. Resuspension of this powder and the powders of Examples 12 through 15 were according to the procedures of Example 6.

Example 12

To this aliquot was added 36 grams of glycerol and 138 ml 31% HCl. After agitation, the pH was read as 4.8.

Example 13

36 grams of glycerol and 12.7 ml HCl were added to the third aliquot to give a final pH of 5.5. Also, one liter of well water was added to make the slurry pumpable.

Example 14

36 grams of glycerol, 8.3 ml 31% HCl and three liters of well water were added to this sample.

Example 15

36 grams of glycerol, 8.3 ml 31% HCl, three liters of well water, and no HCl were added to this sample before spray drying.

The results of the resuspendibility tests at different pH's are given in Table V herein.

Examples 16–20

Effect of Concentration on Resuspendability

Superior resuspendability of this invention over a wide range of concentrations are shown below using $Al_2O_3$-glycerol-HCl co-dried systems. Each of the examples outlined below (Examples 16 through 20) used powder synthesized in accordance with the procedures of Example 7. The results for Examples 16–20 are given in Table VI herein.

Example 16

One gram of Example 7 powder and 25 grams of deionized water were put into a 4"×1" glass vial and shaken ten times. This represented the 2% $Al_2O_3$ example. Except for powder quantities, all resuspensions were performed identically and followed the procedures given in Example 6.

Example 17

This example is a duplicate of Example 7.

Example 18

Three grams of powder gave approximately a 6% $Al_2O_3$ resuspension.

Example 19

Four grams of powder resulted in an 8% resuspension.

Example 20

Five grams of powder resuspended for a 10% $Al_2O_3$ level.

Examples 21–33

Order of Component Addition in Relation To Spray Drying on Resuspendability Resuspendability studies were performed on four different variations of co-dried powders: $Al_2O_3$ alone, $Al_2O_3$ co-dried with glycerol, $Al_2O_3$ co-dried with glycerol and HCl, and $Al_2O_3$ co-dried with HCl. To each of these powders glycerol, HCl, or both were added after spray drying. The resulting thirteen examples examined at 4% and 8% $Al_2O_3$.

5000 grams of 9.6 wt. % $Al_2O_3$ were added to an 18 liter Nalgene polypropylene vessel. Nine liters of well water was added to the gel and the mixture was homogenized with a Premier dispersator for two hours. This batch was then split into two unequal sized aliquots; one, 7625 grams and the other, 6120 grams. The larger portion was acidified to pH 4.8 with 27 ml of 31% HCl in an 8 liter Nalgene polypropylene vessel. The smaller portion received no HCl.

The acidified batch was split into two equal portions of 3800 grams, each put into an 8 liter Nalgene polypropylene vessel. To one of these 3800 gram batches was added 43.4 grams of glycerol. This batch was agitated for one hour. The other 3800 gram batch received no glycerol.

The unacidified half was also split into two aliquots of about 3060 grams each. Again, each was placed in an 8 liter Nalgene polypropylene vessel, One portion received 35.0 gram glycerol according to the formula given for Examples 1–5, and one portion received no glycerol. The regime for Examples 21–33 is given in Table VII herein; the results for Examples 21–33 are given in Tables VIII and IX herein.

The slurries were all spray dried according to Example 1, but 2 liters of well water had to be added to the unacidified slurries to make them pumpable.

Examples 21–26

Spray Dried $Al_2O_3$ Plus UnCo-Dried Adjuvants

Example 21A

To a 4"×1" glass vial containing 25 grams of deionized water was added two grams of $Al_2O_3$ powder as prepared above. The vial was shaken ten times and then 4 drops of 31% HCl were added to the vial by a medicine dropper and shaken again for ten times. The vial was left overnight at which time a pH reading was taken and observations were made. This represented a 4% $Al_2O_3$ sample. Examples 22 through 26 follow the above procedure with the stated changes.

Example 21B

An 8% $Al_2O_3$ sample was also made up with 4 grams of powder in 25 grams of deionized water plus 5 drops HCl.

Example 22A

4% $Al_2O_3$ and 3 drops HCl.

Example 22B

8% $Al_2O_3$ and 4 drops HCl.

Example 23A

4% $Al_2O_3$, 3 drops glycerol (0.2 grams), and 4 drops HCl. Amount of glycerol to each vial was figured according to formula given in Examples 1–5.

Example 23B 8% $Al_2O_3$, 6 drops glycerol (0.4grams), and 5 drops HCl.

Example 24A

4% $Al_2O_3$, 3 drops HCl, 3 drops glycerol.

Example 24B

8% $Al_2O_3$, 4 drops HCl, and 3 drops glycerol.

Example 25A

4% $Al_2O_3$ and 6 drops glycerol.

Example 25B

8% $Al_2O_3$ and 6 drops glycerol.

Example 26A

4% $Al_2O_3$; no additives.

Example 26B

8% $Al_2O_3$; no additives.

Examples 27–29

$Al_2O_3$-glycerol co-dried powder was used in Examples 27 to 29. These resuspensions were prepared according to the procedure in Example 21A.

Example 27A

4% $Al_2O_3$ and 3 drops HCl.

Example 27B

8% $Al_2O_3$ and 4 drops HCl.

Example 28A

4% $Al_2O_3$ and 4 drops HCl.

Example 28B

8% $Al_2O_3$ and 5 drops HCl.

Example 29A

4% $Al_2O_3$; no additives.

Example 29B

8% $Al_2O_3$; no additives.

Examples 30–31

$Al_2O_3$-Glycerol-HCl Co-Dried Systems—No Additives $Al_2O_3$-Glycerol-HCl Co-Dried powder was used in Examples 30A and 30B. These resuspensions also followed the procedure given in Example 21A.

Example 30A

4% $Al_2O_3$

Example 30B

8% $Al_2O_3$

Example 31A

4% $Al_2O_3$ using powder prepared according to Example 11.

Example 31B

8% $Al_2O_3$ using powder prepared according to Example 11.

Examples 32–33

$Al_2O_3$-HCl Co-Dried Systems $Al_2O_3$-HCl Co-Dried powder was used in Examples 32 and 33. These resuspensions followed the procedure given in Example 21A.

Example 32A

4% $Al_2O_3$ and 3 drops glycerol.

Example 32B

8% $Al_2O_3$ and 6 drops glycerol.

Example 33A

4% $Al_2O_3$; no additives.

Example 33B

8% $Al_2O_3$; no additives.

Examples 34–50

Resuspendability of $Al_2O_3$-Adjuvant Co-Dried Systems

Examples 34–50 show the superior resuspendability of $Al_2O_3$ gel co-dried with a number of additives, thirteen of eighteen having a positive effect on resuspendability.

5500 grams of Al$_2$O$_3$ gel and ten liters of well water were slurried with a dispersator in an 18 liter reaction vessel for two hours. Four 4000 gram aliquots were taken from this main batch and each was mixed in four 8-liter reaction vessels. This diluted the gel from 9.6% Al$_2$O$_3$ to 3.4% Al$_2$O$_3$. All slurries possessed 3/1 Al$_2$O$_3$ to additive ratios. Analyses for the powders used in Examples 34–50 are given in Table X herein. The results for Examples 34–50 are given in Tables XI and XII herein.

Example 34A

To one of the 4000 gram aliquots was added 45.5 grams of sucrose according to the formula given for Examples 1–5. The slurry was mixed in a dispersator for one hour. Two liters of additional well water were added to make the gel pumpable. The slurry was then spray dried and resuspended at 4% according to Example 1. The following Examples 35 to 50 follow the above example except that in Examples 38 through 50, 3000 grams of slurry and 34.1 grams of additive were used. The additives utilized were as follows:

sucrose—sucrose USP
lactose—Fisher ACS—lactose
sorbitol—ICI 70% sorbitol solution
polypropylene glycol
Carbowax 200—Union Carbide "CARBOWAX 200"; Grade 1, 2 propanediol
Carbowax 400—Union Carbide "CARBOWAX 400"
Carbowax 600—Union Carbide "CARBOWAX 600"
stearic acid—Baker certified stearic acid
citric acid—Pfizer citric acid USP
potassium citrate—Fisher certified potassium citrate
corn starch—Sargent-Welsh corn starch
Gelatin—Atlantic Gelatin edible 200B
glycine—Walker glycine USP
beta-alanine—Fisher beta-alanine purified grade
L-Glutamic acid—Fisher certified glutamic acid
Veegum—"VEEGUM" regular grade—R.T. Vanderbilt Inc.
Urea—Fisher ACS grade
PVP K-30—General Aniline & Film Corp. PVP (polyvinylpyrolidine) K-30 USP
PVP K-60—General Aniline & Film Corp. PVP (polyvinylpyrolidine)

Examples 51–71

Protein Binding

A known excess of protein standard was mixed with the sample. The non-adsorbed protein was spectrometrically determined and subtracted from the total added protein.

Protein Reagent

A protein reagent was prepared by pipetting 30 ml of deionized water into a 100 ml breaker. 1.596 grams of bovine albumin Fraction V powder, Armour Pharmaceutical Company, was added to the water. The resultant mixture was gently stirred to effect solution. The solution was then filtered through Whatman #4 filter paper and stored in a glass stoppered flask.

Preparation of Standard Curve

Protein reagent as prepared according to the above was pipetted in amounts of 0.5, 1.0, 1.5 and 2.0 ml respectively into four different 50 ml volumetric flasks and each flask was diluted to the mark with deionized water. The four standards were each well mixed. Each standard contained 0.25, 0.50, 0.75 and 1.00 mg. protein per/ml respectively. Absorbance of each standard was obtained at a wavelength of 280 nm using 10 mm silica cells on a Beckman Model 25 spectrophotometer using deionized water as a blank. A standard graph was prepared by plotting absorbance vs. concentration of each protein standard (mg. Protein/ml) on linear graph paper. The best possible straight line to fit most of the points and the origin was drawn.

Procedure

To at least three significant figures two and four grams of the Al$_2$O$_3$ samples were weighed into two separate 50 ml glass stoppered centrifuge tubes (concentration of each sample was approximately 40 mg and 80 mg Al$_2$O$_3$). A sufficient amount of deionized water was added from a burette so that grams of sample plus milliliters of water equaled 17.0 mls (if the density of the suspension was significantly different from one, corrections were made for the sample volume). The samples were shaken gently to disperse the suspension. 3.00 ml (150 mg of protein) of protein reagent (Bovine Albumin F.V, 5% Solution) solution was then added. The tubes were then mixed gently and placed on a Burrell wrist action shaker. The tubes were shaken gently at a setting of 2 for 15 minutes.

The tubes were centrifuged for 15 minutes at 2000 to 2500 RPM. The supernatant was filtered through a millipore HA (0.45 μm) membrane filter paper. 10 ml of clear filtrate was pipetted into a 100 ml volumetric flask and diluted to volume with deionized water. The absorbance for each sample at 280 nm wavelength was read using 10 mm silica cells, the model 25 spectrophotometer and deionized water as a blank. The concentration of each non-adsorbed protein sample was obtained in mg/ml at approximately 40 mg Al$_2$O$_3$ and 80.0 mg Al$_2$O$_3$ level from the standard graph.

Calculations

@approximately 40 mg Al$_2$O$_3$ level, $$\frac{\text{mg Protein adsorbed}}{\text{mg Al}_2\text{O}_3} = 150 - \frac{\text{mg/ml Protein from graph} \times 2 \times 100}{\text{mg. of Al}_2\text{O}_3 \text{ in suspension}}$$

And, approximately 80 mg Al$_2$O$_3$ level, $$\frac{\text{mg Protein adsorbed}}{\text{mg Al}_2\text{O}_3} = 150 - \frac{\text{mg/ml Protein from graph} \times 2 \times 100}{\text{mg of Al}_2\text{O}_3 \text{ in suspension}}$$

Results

The average of both the mg Protein/mg Al$_2$O$_3$ were taken at approximately 40 mg Al$_2$O$_3$ and 80 mg Al$_2$O$_3$ level and reported as mg Protein/mg Al$_2$O$_3$.

Using the above procedure, protein-binding capacities were determined for various co-dried compounds in Examples 51–71 and the results are given in Table XIII herein.

Since surface area plays a major role in the adsorption measured in this test, micronization might increase the values of the co-dried systems and not the Al$_2$O$_3$ dried without additives.

Examples 72–91

Protein Binding

The same test procedure as in Examples 51–71 was utilized in Examples 72–91 except the pH was adjusted to 5.5. The glycerine control (100% glycerine) test was not applicable, since both it and the protein solution were soluble in mixed form.

Figure 1:
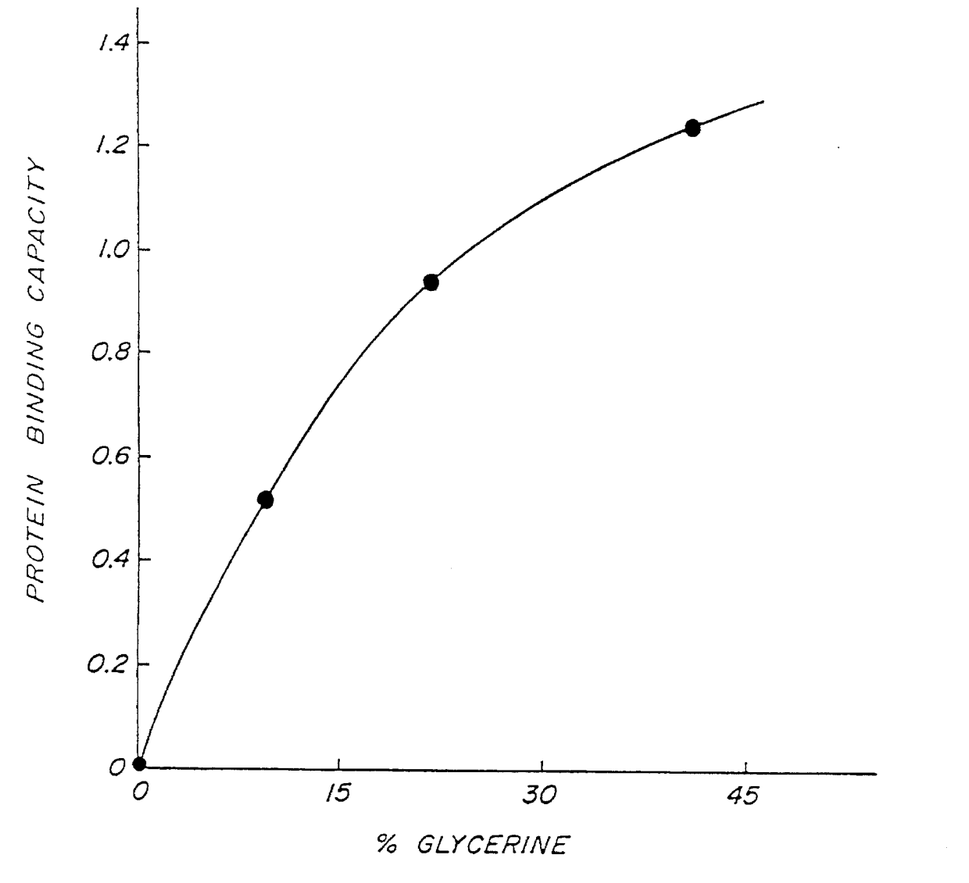
The FIGURE is a plot of protein binding capacity vs. glycerine for co-dried $Al_2O_3$-glycerine powders.

A plot of protein binding capacity vs. % glycerine for co-dried $Al_2O_3$-glycerine without acid is given in the FIGURE (Example Nos. 72–75). The results for Examples 72–91 are given in Table XIV herein.

Examples 92–100

In Examples 92–100, co-dried systems of $Al_2O_3$-glycerine prepared in accordance with this invention were evaluated with and without the addition of acid (HCl). The results for Examples 92–100 are given in Table XV herein. It is evident from Table XV that resuspendability was afforded to only those systems employing acid. The use of acid also increased the protein binding capacity of the co-dried systems.

The present invention may be embodied in other specific forms without departing from the spirit or essential attributes thereof and, accordingly, reference should be made to the appended claims, rather than to the foregoing specification, as indicating the scope of the invention.

TABLE I

| Example No. | % $Al_2O_3$ | $Al_2O_3$/Glycerol Ratio in Slurry |
|---|---|---|
| 1 | 61.4 | 6/1 |
| 2 | 60.1 | 3/1 |
| 3 | 58.6 | 2/1 |
| 4 | 57.9 | 3/2 |
| 5 | 64.47 | 3/0 |

TABLE II

| Example No. | pH Measured | $Al_2O_3$/Glycerol Ratio In Slurry | *Description |
|---|---|---|---|
| 1A | 4.7 | 6/1 | fluid gel |
| 1B | 6.0 | 6/1 | thick fluid gel |
| 2A | 5.1 | 3/1 | gel |
| 2B | 6.3 | 3/1 | gel |
| 3A | 4.7 | 2/1 | fluid gel |
| 3B | 6.3 | 2/1 | gel |
| 4A | 4.0 | 3/2 | fluid gel |
| 4B | 6.3 | 3/2 | gel |
| 5A | 4.7 | 3/1 | fluid gel |
| 5B | 6.2 | 3/0 | with 0.2 cm unsuspended powder |

*All resuspensions described at a minimum of 1 day, maximum of 30 days.

TABLE III

| Example No. | % $Al_2O_3$ | % Glycerol | $Al_2O_3$/Glycerol Ratio Slurry | $Al_2O_3$/Glycerol Ratio Powder |
|---|---|---|---|---|
| 6 | 62.18 | 10.5 | 6/1 | 5.9/1 |
| 7 | 59.20 | 16.5 | 3/1 | 3.6/1 |
| 8 | 56.70 | 19.7 | 2/1 | 2.9/1 |
| 9 | 55.77 | 22.9 | 3/2 | 4.9/2 |
| 10 | 64.47 | — | 3/0 | 3/0 |

TABLE IV

| Example No. | Measured pH | Description |
|---|---|---|
| 6 | 5.8 | gel |
| 7 | 5.8 | gel |
| 8 | 5.6 | gel |
| 9 | 5.7 | gel |
| 10 | 5.9 | 0.5 cm unsuspended powder in 6 cm supernatant |

TABLE V

| Example No. | Measured pH | $Al_2O_3$/Glycerol in Slurry | Description |
|---|---|---|---|
| 11 | 5.5 | 3/1 | gel |
| 12 | 5.9 | 3/1 | gel |
| 13 | 6.4 | 3/1 | fluid gel |
| 14 | 7.2 | 3/1 | 0.5 cm unsuspended powder and 6 cm supernatant |
| 15 | 7.9 | 3/1 | same as Example 14 |

TABLE VI

| Example No. | Measured PH | Approx. % $Al_2O_3$ Concentration in Vial | Description |
|---|---|---|---|
| 16 | 5.7 | 2 | fluid gel |
| 17 | 5.7 | 4 | gel |
| 18 | 5.7 | 6 | gel |
| 19 | 5.8 | 8 | very thick gel |
| 20 | 5.7 | 10 | very thick gel |

TABLE VII

```
              Al₂O₃ Gel + well water
              /                    \
         unacidified              acidified
         /        \               /        \
    glycerol   no glycerol   glycerol   no glycerol
       |           |             |           |
  Al₂O₃ +       Al₂O₃       Al₂O₃ +       Al₂O₂ + HCl
  glycerol                   glycerol + HCl pH of 4%    pH of 4%      pH of 4%      pH of 4%
resuspension  resuspension  resuspension  resuspension
  = 9.0        = 8.6         = 6.9         = 6.6
```

TABLE VIII

| Example No. | Measured pH | % Al₂O₃ | Resuspension | Description |
|---|---|---|---|---|
| 21A | 4.6 | 4 | fair | 0.5 cm settled powder below hazy liquid |
| 21B | 5.0 | 8 | fair | 2 cm clear liquid above unsuspended powder |
| 22A | 5.5 | 4 | fair | 1 cm settled powder above hazy liquid |
| 22B | 6.2 | 8 | fair | 2 cm clear liquid above unsuspended powder |
| 23A | 4.2 | 4 | fair | 0.5 cm settled powder below hazy powder |
| 23B | 5.7 | 8 | good | thick suspension |
| 24A | 5.2 | 4 | fair | 1.5 cm settled powder below hazy liquid |
| 24B | 6.2 | 8 | fair | 1.5 cm clear liquid above settled powder |
| 25A | 8.4 | 4 | no | unsuspended powder |
| 25B | 8.5 | 8 | no | unsuspended powder |
| 26A | 8.5 | 4 | no | unsuspended powder |
| 26B | 8.4 | 8 | no | unsuspended powder |
| 27A | 5.2 | 4 | good | gel |
| 27B | 6.5 | 8 | good | very thick gel |
| 28A | 4.1 | 4 | good | fluid gel |
| 28B | 6.2 | 8 | good | very thick qel |
| 29A | 8.9 | 4 | no | unsuspended powder |
| 29B | 8.9 | 8 | no | unsuspended powder |
| 30A | 6.3 | 4 | no | unsuspended powder |
| 30B | 6.5 | 8 | no | unsuspended powder |
| 31A | 5.6 | 4 | good | gel |
| 31B | 5.8 | 8 | good | very thick gel |
| 32A | 6.3 | 4 | no | unsuspended powder |
| 32B | 6.5 | 8 | no | unsuspended powder |
| 33A | 6.3 | 4 | no | unsuspended powder |
| 33B | 6.5 | 8 | no | unsuspended powder |

*All descriptions made at minimum 1 day, maximum 30 days.

TABLE IX

Reevaluation Of Resuspendability Taken About Six Weeks Later Than Those Taken In Table VIII

| Example No. | % Al₂O₃ | Resuspension | *Description |
|---|---|---|---|
| 21A | 4 | good | gel |
| 21B | 8 | good | gel |
| 22A | 4 | fair | 1.5 cm clear liquid above 4 cm resuspended powder |
| 22B | 8 | fair | 0.5 cm clear liquid above 5 cm resuspended powder |
| 23A | 4 | good | gel |
| 23B | 8 | good | gel |
| 24A | 4 | good | fluid gel |
| 24B | 8 | fair | 1 cm clear liquid above 4.5 cm resuspended powder |
| 25A | 4 | no | unsuspended powder |
| 25B | 8 | no | unsuspended powder |
| 26A | 4 | no | unsuspended powder |
| 26B | 8 | no | unsuspended powder |
| 27A | 4 | good | gel |
| 27B | 8 | good | very thick gel |
| 28A | 4 | good | gel |
| 28B | 8 | good | very thick gel |
| 29A | 4 | no | unsuspended powder |
| 29B | 8 | no | unsuspended powder |
| 30A | 4 | fair | 1 cm clear liquid above 4.5 cm resuspended powder |
| 30B | 8 | fair | 1.5 cm clear liquid above 4 cm resuspended powder |
| 31A | 4 | good | gel |
| 31B | 8 | good | very thick gel |
| 32A | 4 | no | unsuspended powder |
| 32B | 8 | no | unsuspended powder |

*All descriptions made at minimum 1 day, maximum 30 days.

TABLE X

| Additive | % Al₂O₃ |
|---|---|
| none | 65.31 |
| sucrose | 56.07 |
| lactose | 56.36 |

TABLE X-continued

| Additive | % Al$_2$O$_3$ |
| --- | --- |
| sorbitol | 56.74 |
| propylene glycol | 63.74 |
| urea | 59.29 |
| Carbowax 600 | 56.83 |
| Carbowax 400 | 56.42 |
| Veegum | 54.40 |
| corn starch | 51.26 |
| PVP K-30 | 55.35 |
| citric acid | 57.66 |
| stearic acid | 63.66 |
| gelatin | 57.75 |
| PVP K-60 | 55.68 |
| Carbowax 200 | 54.21 |
| glycine | 58.61 |
| L-glutamic acid | 58.72 |
| beta-alanine | 58.46 |
| potassium citrate | 56.97 |

TABLE XI

| Example No. | Additive | Wt. % Al$_2$O$_3$ Resuspension | Drops HCl (31%) Added |
| --- | --- | --- | --- |
| 34B | sucrose | 8 | 3 (0.14 g) |
| 34C | sucrose | 4 | 3 |
| 34D | sucrose | 8 | 5 (0.24 g) |
| 35A | lactose | 4 | 3 |
| 35B | lactose | 8 | 5 |
| 35C | lactose | 4 | 3 |
| 35D | lactose | 8 | 3 |
| 36A | sorbitol | 4 | 3 |
| 36B | sorbitol | 8 | 5 |
| 36C | sorbitol | 4 | 3 |
| 36D | sorbitol | 8 | 3 |
| 37A | propylene glycol | 4 | 3 |
| 37B | propylene glycol | 8 | 5 |
| 37C | propylene glycol | 4 | 3 |
| 37D | propylene glycol | 8 | 3 |
| 38A | Carbowax 200 | 4 | 3 |
| 38B | Carbowax 200 | 8 | 3 |
| 38C | Carbowax 200 | 4 | 3 |
| 38D | Carbowax 200 | 8 | 5 |
| 39A | Carbowax 400 | 4 | 3 |
| 39B | Carbowax 400 | 8 | 5 |
| 39C | Carbowax 400 | 4 | 3 |
| 39D | Carbowax 400 | 8 | 3 |
| 40A | Carbowax 600 | 4 | 3 |
| 40B | Carbowax 600 | 8 | 5 |
| 40C | Carbowax 600 | 4 | 3 |
| 40D | Carbowax 600 | 8 | 3 |
| 41A | stearic acid | 4 | 3 |
| 41B | stearic acid | 8 | 5 |
| 41C | stearic acid | 4 | 3 |
| 41D | stearic acid | 8 | 3 |
| 42A | citric acid | 4 | 5 |
| 42B | citric acid | 8 | 3 |
| 42C | citric acid | 4 | 3 |
| 42D | citric acid | 8 | 3 |
| 43A | potassium citrate | 4 | 3 |
| 43B | potassium citrate | 8 | 5 |
| 43C | potassium citrate | 8 | 3 |
| 44A | corn starch | 4 | 3 |
| 44B | corn starch | 8 | 5 |
| 44C | corn starch | 4 | 3 |
| 44D | corn starch | 8 | 3 |
| 45A | urea | 4 | 5 |
| 45B | urea | 8 | 3 |
| 45C | urea | 4 | 3 |
| 45D | urea | 8 | 3 |
| 46A | glycine | 4 | 3 |
| 46B | glycine | 8 | 5 |
| 46C | glycine | 4 | 3 |
| 46D | glycine | 8 | 3 |
| 47A | beta-alanine | 4 | 3 |
| 47B | beta-alanine | 8 | 5 |
| 47C | beta-alanine | 4 | 3 |
| 47D | beta-alanine | 8 | 3 |
| 48A | L-glutamic acid | 4 | 3 |
| 48B | L-glutamic acid | 8 | 5 |
| 48C | L-glutamic acid | 4 | 0 |
| 48D | L-glutamic acid | 8 | 3 |
| 49A | gelatin | 4 | 3 |
| 49B | gelatin | 8 | 5 |
| 49C | gelatin | 4 | 3 |
| 50A | Veegum | 4 | 3 |
| 50B | Veegum | 8 | 5 |
| 50C | Veegum | 4 | 3 |
| 50D | Veegum | 8 | 3 |

TABLE XII

| Example No. | Additive | Adjusted pH | % Al$_2$O$_3$ | Resuspension | *Description |
| --- | --- | --- | --- | --- | --- |
| 34A | sucrose | 5.2 | 4 | good | thick gel |
| 34B | sucrose | 6.7 | 8 | good | fluid gel |
| 34C | sucrose | 6.0 | 4 | good | thick gel |
| 34D | sucrose | 5.6 | 8 | good | very thick gel |
| 35A | lactose | 5.5 | 4 | good | thick gel |
| 35B | lactose | 5.6 | 8 | good | thick gel |
| 35C | lactose | 6.3 | 4 | good | thick fluid gel |
| 35D | lactose | 6.6 | 8 | good | fluid gel |
| 36A | sorbitol | 5.5 | 4 | good | gel |
| 36B | sorbitol | 6.4 | 8 | good | very thick gel |
| 36C | sorbitol | 6.3 | 4 | good | fluid gel |
| 36D | sorbitol | 6.5 | 8 | good | gel |
| 37A | propylene glycol | 5.2 | 4 | good | gel |
| 37B | propylene | 6.5 | 8 | fair | 0.5 cm clear |

TABLE XII-continued

| Example No. | Additive | Adjusted pH | % Al₂O₃ | Resuspension | *Description |
|---|---|---|---|---|---|
| | glycol | | | | liquid on 5 cm powder |
| 37C | propylene glycol | 6.5 | 4 | no | unsuspended powder |
| 37D | propylene glycol | 6.7 | 8 | fair | 0.5 cm clear liquid on 5 cm powder |
| 38A | Carbowax 200 | 5.5 | 4 | good | thick fluid gel |
| 38B | Carbowax 200 | 6.4 | 8 | good | thick fluid gel |
| 38C | Carbowax 200 | 5.8 | 4 | good | gel |
| 38D | Carbowax 200 | 5.6 | 8 | good | gel |
| 39A | Carbowax 400 | 4.6 | 4 | good | thick fluid gel |
| 39B | Carbowax 400 | 6.1 | 8 | good | very thick gel |
| 39C | Carbowax 400 | 6.0 | 4 | good | gel |
| 39D | Carbowax 400 | 6.4 | 8 | good | thick fluid gel |
| 40A | Carbowax 600 | 4.7 | 4 | good | thick fluid gel |
| 40B | Carbowax 600 | 5.1 | 8 | good | gel |
| 40C | Carbowax 600 | 5.4 | 4 | good | thick fluid gel |
| 40D | Carbowax 600 | 6.2 | 8 | no | unsuspended powder |
| 41A | stearic acid | 4.1 | 4 | no | unsuspended powder with hazy liquid |
| 41B | stearic acid | 5.1 | 8 | no | same as above |
| 41C | stearic acid | 4.3 | 4 | no | same as above |
| 41D | stearic acid | 5.2 | 8 | no | same as above |
| 42A | citric acid | 2.5 | 4 | no | unsuspended powder |
| 42B | citric acid | 2.5 | 8 | no | same as above |
| 42C | citric acid | 2.6 | 4 | no | same as above |
| 42D | citric acid | 2.7 | 8 | no | same as above |
| 43A | potassium citrate | 5.8 | 4 | no | same as above |
| 43B | potassium citrate | 6.6 | 8 | no | same as above |
| 43C | potassium citrate | 8.3 | 8 | no | same as above |
| 44A | corn starch | 4.8 | 4 | good | fluid gel |
| 44B | corn starch | 5.1 | 8 | good | thick fluid gel |
| 44C | corn starch | 6.1 | 4 | no | unsuspended powder |
| 44D | corn starch | 6.2 | 8 | no | same as above |
| 45A | urea | 4.9 | 4 | good | fluid gel |
| 45B | urea | 5.7 | 8 | good | very thick gel |
| 45C | urea | 5.6 | 4 | good | thick gel |
| 45D | urea | 6.5 | 8 | no | unsuspended powder |
| 46A | glycine | 5.2 | 4 | good | gel |
| 46B | glycine | 5.4 | 8 | good | gel |
| 46C | glycine | 5.6 | 4 | good | gel |
| 46D | glycine | 6.6 | 8 | fair | 1 cm clear liquid above 4.5 cm powder |
| 47A | beta-alanine | 5.0 | 4 | good | fluid gel |
| 47B | beta-alanine | 6.0 | 8 | good | gel |
| 47C | beta-alanine | 6.2 | 4 | good | gel |
| 47D | beta-alanine | 6.7 | 8 | fair | 0.5 cm clear liquid above powder |
| 48A | L-glutamic acid | 3.7 | 4 | good | gel |
| 48B | L-glutamic acid | 3.9 | 8 | good | thick fluid gel |
| 48C | L-glutamic | 4.9 | 4 | no | unsuspended powder |
| 48D | L-glutamic | 4.1 | 8 | good | thick fluid |

TABLE XII-continued

| Example No. | Additive | Adjusted pH | % Al$_2$O$_3$ | Resuspension | *Description |
|---|---|---|---|---|---|
| | | | | | gel |
| 49A | gelatin | 5.3 | 4 | no | same as above |
| 49B | gelatin | 6.1 | 8 | no | same as above |
| 49C | gelatin | 6.6 | 8 | no | same as above |
| 50A | Veegum | 5.5 | 4 | no | same as above |
| 50B | Veegum | 6.3 | 8 | no | same as above |
| 50C | Veegum | 6.6 | 4 | no | same as above |
| 50D | Veegum | 6.7 | 8 | no | same as above |

TABLE XIII

Protein Binding Capacity of Al$_2$O$_3$ with Additives*

| Example No. | Sample Description | % Al$_2$O$_3$ | mg. of Protein adsorbed mg. of Al$_2$O$_3$ |
|---|---|---|---|
| 51 | Al$_2$O$_3$ slurry (no additive) | 3.37 | 1.34 |
| 52 | Al$_2$O$_3$ w/L-glutamic acid | 58.72 | 0.48 |
| 53 | Al$_2$O$_3$ w/Carbowax-600 | 56.83 | 0.25 |
| 54 | Al$_2$O$_3$ w/beta-alanine | 58.46 | 0.24 |
| 55 | Al$_2$O$_3$ w/Carbowax-400 | 56.42 | 0.21 |
| 56 | Al$_2$O$_3$ w/stearic acid | 63.62 | 0.20 |
| 57 | Al$_2$O$_3$ w/K-citrate | 56.92 | 0.20 |
| 58 | Al$_2$O$_3$ w/citric acid | 57.66 | 0.17 |
| 59 | Al$_2$O$_3$ w/Glycine | 58.61 | 0.17 |
| 60 | Al$_2$O$_3$ w/propylene glycol | 63.74 | 0.14 |
| 61 | Al$_2$O$_3$ w/urea | 59.29 | 0.13 |
| 62 | Al$_2$O$_3$ w/sucrose | 56.07 | 0.12 |
| 63 | Al$_2$O$_3$ w/Carbowax-200 | 59.21 | 0.12 |
| 64 | Al$_2$O$_3$ (No additive) | 65.31 | 0.11 |
| 65 | Al$_2$O$_3$ w/sorbitol | 56.74 | 0.11 |
| 66 | Al$_2$O$_3$ w/gelatin | 57.75 | 0.10 |
| 67 | Al$_2$O$_3$ w/PVP (K-60) | 55.68 | 0.09 |
| 68 | Al$_2$O$_3$ w/PVP (K-30) | 55.35 | 0.08 |
| 69 | Al$_2$O$_3$ w/lactose | 56.36 | 0.04 |
| 70 | Al$_2$O$_3$ w/Veegum | 54.40 | 0.0 |
| 71 | Al$_2$O$_3$ w/corn starch | 51.26 | 0.0 |

*Al$_2$O$_3$ powder with 3:1 additive ratio

TABLE XIV

| Example No. | Co-Dried Additive | % Al$_2$O$_3$ | % Additive | Approx. Al$_2$O$_3$ | Actual Al$_2$O$_3$ | Nat'l pH | PB @ Nat'l pH mg Protein mg Al$_2$O$_3$ | PB @* pH 5.51 mg Protein mg Al$_2$O$_3$ |
|---|---|---|---|---|---|---|---|---|
| 72 | None | 65.3 | 0 | — | — | 8.6 | 0.11 | 0 |
| 73 | Glycerine | 61.4 | 10.75 | 6/1 | 5.7/1 | | 0.09 | 0.54 |
| 74 | Glycerine | 60.1 | 21.5 | 3/1 | 2.8/1 | 8.5 | 0.11 | 0.95 |
| 75 | Glycerine | 57.9 | 43 | 1.5/1 | 1.3/1 | | 0.26 | 1.25 |
| 76 | Glycerine/HCl | | | 3/1 | | 5.5 | 1.7 | 1.7 |
| 77 | Glycerine/HCl | 62.1 | 15.7 | | 4.0/1 | 4.7 | | 1.7 |
| 78 | None | 65.3 | 0 | — | — | 8.6 | 0.11 | 0 |
| 79 | Glycerine | 60.1 | 21.6 | 3/1 | 2.8/1 | 8.5 | 0.11 | 0.95 |
| 80 | Carbowax 400 | 56.4 | | 3/1 | | 8.1 | 0.21 | 0.73 |
| 81 | Lactose | 56.4 | | 3/1 | | 8.8, 8.7 | 0.04 | 0.67 |
| 82 | Glycine | 58.6 | | 3/1 | | 8.1 | 0.17 | 0.58 |
| 83 | Sorbitol | 56.7 | | 3/1 | | 8.8, 8.7 | 0.11 | 0.36 |
| 84 | Propylene glycol | 63.7 | | 3/1 8.6 | | 8.7, | 0.14 | 0.34 |
| 85 | Citric Acid | 57.7 | | 3/1 | | 3.4 | 0.17 | 0.01 |
| 86 | Stearic Acid | 63.6 | | 3/1 | | 7.8 | 0.20 | 0.05 |
| 87 | Corn Starch | 51.3 | | 3/1 | | 8.2 | 0 | 0 |
| 88 | Gelatin | 57.8 | | 3/1 | | 8.0 | 0.10 | 0 |
| 89 | K Citrate | 57.0 | | 3/1 | | 9.4 | 0.20 | 0.1. |
| 90 | Arlacel 165** | 58.0 | | 3/1 | | 8.2 | | 0 |
| 91 | Arlacel 165** | 55.9 | | 3/1 | | | | 0.17 |

*Adjusted with HCl or caustic to yield pH 5.51
**Arlacel 165 - 95% glycerol monostearate and 5% polyethylene glycol monostearate

TABLE XV

Examples 92–100
Co-Dried Al$_2$O$_3$ and Glycerol - With and Without HCl

| Example No. | HCl | Al$_2$O$_3$/Glycerol Ratio in Slurry | % Al$_2$O$_3$ in Powder | Protein Binding mg Protein/ mg Al$_2$O$_3$ | pH of 4% Al$_2$O$_3$ Suspension | Resuspendability |
|---|---|---|---|---|---|---|
| 92  | No HCl | 3/1   | 58.9  | 0.04 | 9.0  | Poor |
| 93  | No HCl | 3/0.5 | 61.4  | 0.09 | 8.5  | Poor |
| 94  | No HCl | 3/1   | 60.1  | 0.11 | 8.5  | Poor |
| 95  | No HCl | 3/1.5 | 58.6  | 0.15 | 8.5  | Poor |
| 96  | No HCl | 3/2   | 57.9  | 0.26 | 8.5  | Poor |
| 97  | No HCl | 3/1   | 62.48 | 0.4  | 8.5  | Poor |
| 98  | HCl    | 3/1   | 62.48 | 1.7  | 4.7* | Good |
| 99  | HCl    | 3/1   | —     | 1.6  | *    | Good |
| 100 | HCl    | 3/1   | 58.13 | 1.78 | 6.2  | Good |

*pH was adjusted to 5.5 before protein binding test

We claim:

1. A method for the preparation of adsorptive, protein-binding aluminum oxyhydroxides which comprises mixing a carbonate-free, highly hydrated, aluminum oxyhydroxide-containing aqueous suspension, which is relatively inert towards weak alkalis and acids, with an additive, said additive being soluble in water and furnishing coordinating moieties with aluminum, drying said mixture to form solid particles of adsorptive, protein-binding aluminum oxyhydroxide, which are resuspendable when acidified in water, and mixing water with the dried solid particles of aluminum oxyhydroxide and acidifying the resulting mixture to a pH value of between about 4 and about 6.5 to produce resuspended adsorptive, protein-binding, aluminum oxyhydroxide.

2. The method of claim 1 wherein said additive is selected from the group consisting of polyhydric alcohols, sugars, amino acids, polysaccharides and urea.

3. The method of claim 1 wherein said additive is added such that the weight ratio of said aluminum oxyhydroxide, calculated as aluminum oxide, to said additive in said suspension before drying, is between about 10:1 and about 3:2.

4. The method of claim 1 wherein said mixture is dried such that the weight percent of said aluminum oxyhydroxide, calculated as aluminum oxide, is between about 55 weight percent and about 65 weight percent.

5. The method according to claim 1 further comprising the step of incorporating the solid particles of adsorptive, protein-binding aluminum oxyhydroxide into a topical skin composition.

6. The method of claim 1 wherein the pH value is between about 5 and 6.

7. A method for preparation of adsorptive, protein-binding aluminum oxyhydroxides which comprises mixing a carbonate-free, highly hydrated, aluminum oxyhydroxide-containing aqueous suspension, which is relatively inert towards weak alkalis and acids, with an additive selected from the group consisting of polyhydric alcohols, sugars, amino acids, polysaccharides and urea, said additive being soluble in water and furnishing coordinating moieties with aluminum, acidifying the suspension to a pH value of between about 4 and about 6.5, and drying said mixture to form solid particles of adsorptive, protein-binding aluminum oxyhydroxide which are resuspendable in water.

8. The method of claim 7 wherein said pH is between about 5 and about 6.

9. The method of claim 7 wherein said acidification occurs prior to mixing said aluminum oxyhydroxide suspension with said additive to produce a resuspendable, adsorptive, protein-binding, aluminum oxyhydroxide.

10. The method of claim 7 wherein said acidification occurs after mixing said aluminum oxyhydroxide suspension with said additive.

11. The method of claim 7 wherein said additive is added such that the weight ratio of said aluminum oxyhydroxide, calculated as aluminum oxide, to said additive in said suspension before drying, is between about 10:1 and about 3:2.

12. The method of claim 7 wherein said mixture is dried such that the weight percent of said aluminum oxyhydroxide, calculated as aluminum oxide, is between about 55 weight percent and about 65 weight percent.

13. The method according to claim 7 further comprising the step of incorporating the resuspendable, adsorptive, protein-binding aluminum oxyhydroxide into a topical skin composition.

* * * * *